United States Patent
Eiermann et al.

(10) Patent No.: US 7,162,896 B2
(45) Date of Patent: Jan. 16, 2007

(54) APPARATUS FOR CHECKING THE FORMATION OF SCALE, AND WATER-CARRYING APPLIANCE

(75) Inventors: Rüdiger Eiermann, Syrgenstein (DE); Helmut Jerg, Giengen (DE)

(73) Assignee: BSH Bosch und Siemens Hausgeraete GmbH, Munich (DE)

( * ) Notice: Subject to any disclaimer, the term of this patent is extended or adjusted under 35 U.S.C. 154(b) by 0 days.

(21) Appl. No.: 10/926,931

(22) Filed: Aug. 26, 2004

(65) Prior Publication Data
US 2005/0046826 A1    Mar. 3, 2005

Related U.S. Application Data

(63) Continuation of application No. PCT/EP03/01328, filed on Feb. 11, 2003.

(30) Foreign Application Priority Data
Feb. 26, 2002    (DE)    ................ 102 08 214

(51) Int. Cl.
   *B08B 13/00*    (2006.01)
(52) U.S. Cl. .......... 68/56 D; 134/57 D; 134/58 D; 134/113
(58) Field of Classification Search ............. 134/56 D, 134/57 D, 58 D, 113
   See application file for complete search history.

(56) References Cited

U.S. PATENT DOCUMENTS

| | | | |
|---|---|---|---|
| 3,431,411 A * | 3/1969 | Harrick ................. 250/339.12 |
| 3,662,186 A * | 5/1972 | Karklys ...................... 307/141 |
| 3,732,074 A * | 5/1973 | Feitler, Jr. ....................... 436/6 |
| 3,870,417 A * | 3/1975 | Bashark ....................... 356/442 |
| 3,888,269 A * | 6/1975 | Bashark ................... 134/57 D |
| 3,896,827 A * | 7/1975 | Robinson ..................... 134/10 |
| 4,045,668 A * | 8/1977 | Pitt et al. ............... 250/227.25 |
| 4,166,702 A * | 9/1979 | Okamoto et al. ............. 399/57 |
| 4,222,670 A * | 9/1980 | Koshiishi .................... 356/414 |
| 4,552,454 A * | 11/1985 | Glaser et al. .............. 356/4.02 |

(Continued)

FOREIGN PATENT DOCUMENTS

DE    35 43 155    *    6/1986

(Continued)

OTHER PUBLICATIONS

Europena Patent Office 0 966 914 Jun. 1999.*

(Continued)

*Primary Examiner*—Frankie L. Stinson
(74) *Attorney, Agent, or Firm*—Russell W. Warnock; Craig J. Loest

(57) ABSTRACT

An apparatus allows monitoring the formation of scale. The apparatus makes it possible to determine the degree of water hardness or a tendency of the degree of water hardness to change over time and to take measures for adjusting the desired degree of water hardness accordingly. A translucent or transparent element has two end surfaces, at least one element emitting an optical signal, and at least one element receiving an optical signal. The element emitting the optical signal and the element receiving the optical signal are directly adjacent to the end surfaces of the transparent element, and the end surfaces are disposed such that they remain free of scale build-up at all times.

8 Claims, 4 Drawing Sheets

U.S. PATENT DOCUMENTS

| | | | |
|---|---|---|---|
| 4,880,990 A * | 11/1989 | Rando | 250/577 |
| 5,001,938 A * | 3/1991 | Downie | 73/864.34 |
| 5,047,626 A * | 9/1991 | Bobb et al. | 250/227.19 |
| 5,087,823 A * | 2/1992 | Silvy et al. | 250/573 |
| 5,101,851 A * | 4/1992 | Abadi et al. | 137/91 |
| 5,341,661 A * | 8/1994 | Dausch et al. | 68/207 |
| 5,452,076 A * | 9/1995 | Schopper et al. | 356/128 |
| 5,477,576 A * | 12/1995 | Berkcan | 8/158 |
| 5,536,663 A * | 7/1996 | Mueller-Kirschbaum et al. | 436/55 |
| 5,589,935 A * | 12/1996 | Biard | 356/339 |
| 5,611,867 A * | 3/1997 | Cooper et al. | 134/18 |
| 5,729,025 A * | 3/1998 | Erickson et al. | 250/574 |
| 5,800,628 A * | 9/1998 | Erickson et al. | 134/18 |
| 5,923,432 A * | 7/1999 | Kral | 356/432 |
| 5,926,269 A | 7/1999 | Von Der Eltz et al. | |
| 6,084,665 A * | 7/2000 | Trainer | 356/244 |
| 6,300,638 B1 | 10/2001 | Groger et al. | |
| 6,464,798 B1 * | 10/2002 | Rosenbauer et al. | 134/18 |
| 6,494,964 B1 * | 12/2002 | Jacobs et al. | 134/18 |
| 6,509,558 B1 * | 1/2003 | Loch et al. | 250/222.2 |
| 6,544,344 B1 * | 4/2003 | Hegeman et al. | 134/18 |
| 6,819,811 B1 * | 11/2004 | Goldstein | 385/12 |
| 6,880,402 B1 * | 4/2005 | Couet et al. | 73/579 |
| 6,891,606 B1 * | 5/2005 | Smith et al. | 356/70 |
| 6,924,499 B1 * | 8/2005 | Poisel et al. | 250/574 |
| 2002/0066873 A1 | 6/2002 | Poisel et al. | |

FOREIGN PATENT DOCUMENTS

| | | | |
|---|---|---|---|
| DE | 196 26 203 A1 | | 1/1998 |
| DE | 197 14 695 A1 | | 10/1998 |
| DE | 197 40 266 A1 | | 3/1999 |
| DE | 198 25 981 A1 | | 12/1999 |
| EP | 0 966 914 A2 | | 12/1999 |
| EP | 0 972 486 A1 | | 1/2000 |
| GB | 2 105 034 | * | 3/1983 |
| JP | 59-23221 | * | 2/1984 |
| JP | 59-34135 | * | 2/1984 |
| JP | 60-135749 | * | 7/1985 |
| JP | 3-258385 | * | 11/1991 |
| JP | 6-22897 | * | 2/1994 |
| JP | 6-86906 | * | 3/1994 |
| WO | 00/46572 | | 8/2000 |

OTHER PUBLICATIONS

European Patent Office 0 370 238 May 1990.*
European Patent Office 1 180 344 Aug. 2001.*

* cited by examiner

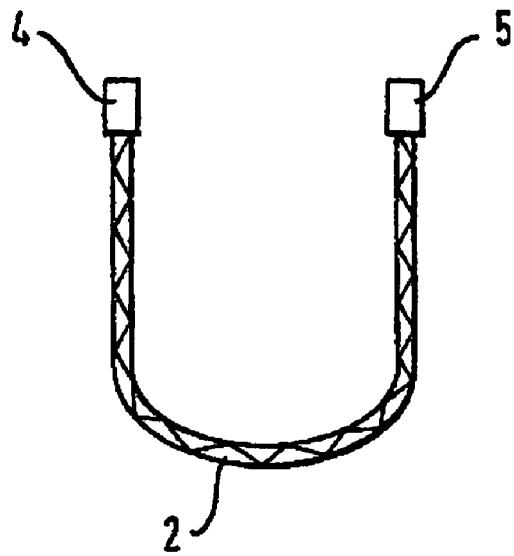
Fig. 1
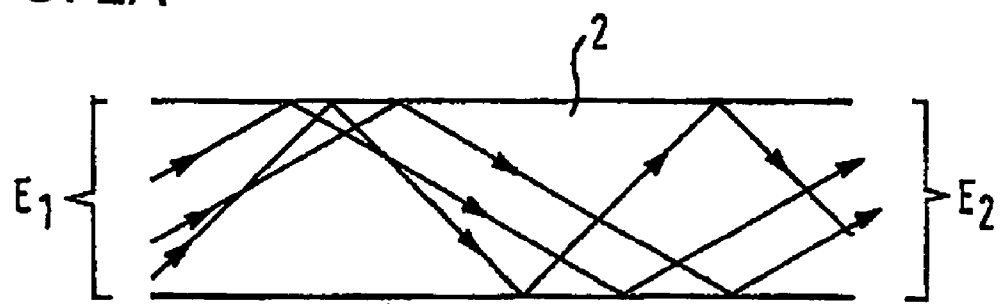
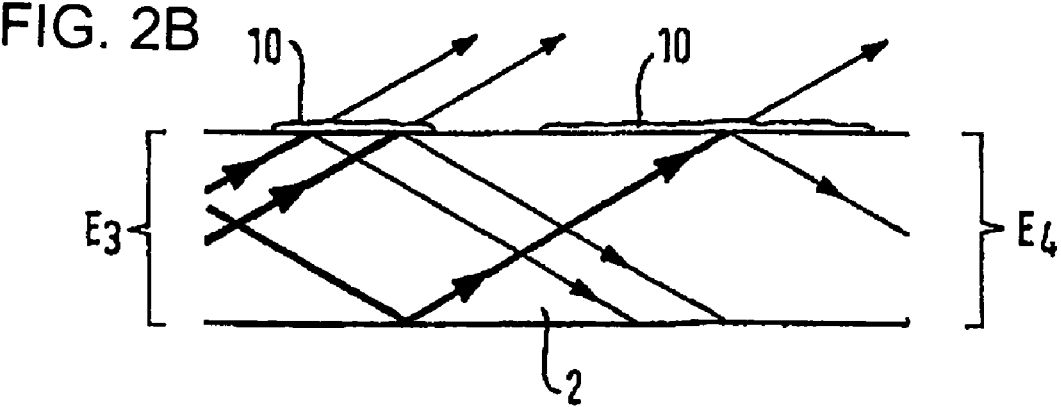

APPARATUS FOR CHECKING THE FORMATION OF SCALE, AND WATER-CARRYING APPLIANCE

CROSS-REFERENCE TO RELATED APPLICATION

This is a continuing application, under 35 U.S.C. § 120, of copending international application No. PCT/EP03/01328, filed Feb. 11, 2003, which designated the United States; this application also claims the priority, under 35 U.S.C. § 119, of German patent application No. 102 08 214.6, filed Feb. 26, 2002; the prior applications are herewith incorporated by reference in their entirety.

BACKGROUND OF THE INVENTION

Field of the Invention

The present invention relates to an apparatus for checking the formation of scale, comprising a translucent element with two terminating surfaces, and also comprising at least one optical-signal-emitting element and at least one optical-signal-receiving element, and to a water-carrying appliance, in particular for domestic use.

For the use of water-carrying household appliances, in particular household dishwashers, the washing liquid is softened in a water-softening configuration, prior to each washing operation, in regions with a high degree of water hardness. If use is made of insufficiently softened water, characteristic lime deposits form, during the drying operation, on the articles which are to be washed. These deposits detract from the appearance, in particular, of glasses and shiny stainless-steel surfaces. In order to avoid these lime deposits, the ion exchanger is usually regenerated on a regular basis, with the result that no lime deposits may be expected in the washing operation following the regenerating operation. Since the softening quality of the ion exchanger decreases on a constant basis between the regenerating operations, and the frequency of scale build-up thus increases, it is desirable for a tendency toward scale build-up and density to be detected in good time, in order for appropriate regenerating measures to be taken.

German published patent application DE 198 25 981 discloses a process and an apparatus for softening water in a program-controlled water-carrying household appliance. There, during one sub-program, a regenerating operation for an ion exchanger is carried out by virtue of a quantity of brine being added and, during a further sub-program, a washing program is carried out.

For carrying out the prior art process, a change in the water hardness as a result of lime deposits on a translucent surface is measured by a sensor with an optical-signal-emitting element and an optical-signal-receiving element. A point in time for carrying out the regenerating operation is determined in dependence on the lime deposit measured, a control unit processing the signals correspondingly and initiating a regenerating operation.

It has proven to be disadvantageous in the case of the prior art apparatus that, in addition to lime deposits on the translucent surface giving corresponding measured values, it is also the case that particles of dirt and other elements of dirt extending over a relatively large surface area adversely affect the path of radiation between the emitting and receiving elements and thus result in falsified measurement results. It has also proven to be disadvantageous that even opacity of the lens of the optical-signal-emitting elements and/or of the optical-signal-receiving elements give measured values, even if the optical properties of the translucent surface remain unchanged, which point to the fact that regeneration is required.

SUMMARY OF THE INVENTION

It is accordingly an object of the invention to provide a device for checking for scale buildup and a water-conducting appliance which overcome the above-mentioned disadvantages of the heretofore-known devices and methods of this general type and which make it possible to determine the formation of scale or a tendency towards the formation of scale and to achieve corresponding measures for setting the desired formation of scale.

With the foregoing and other objects in view there is provided, in accordance with the invention, an apparatus for checking a formation of scale, comprising:

a translucent element formed with first and second terminating surfaces;

at least one optical-signal-emitting element disposed at and directly adjoining the first terminating surface; and at least one optical-signal-receiving element disposed at and adjoining the second terminating surface;

wherein the terminating surfaces are disposed to not be subject to scale deposits.

In other words, the apparatus according to the invention for checking the formation of scale, comprising a translucent element with two terminating surfaces, also has at least one optical-signal-emitting element and at least one optical-signal-receiving element. The translucent element is configured such that the optical-signal-emitting and the optical-signal-receiving elements each directly adjoins a respective one of the terminating surfaces of the translucent elements, and the terminating surfaces are protected so that remain free of scale.

The translucent element is advantageously a rod-like design or, starting from a rod shape, of helical design. The translucent element is expediently arranged in a chamber region, the chamber region having at least one opening which opens out into an interior of a water-carrying household appliance, preferably of a dishwashing compartment, and also having a valve which is suitable for emptying the chamber region.

The valve in the chamber region is expediently operated electromagnetically, it preferably being possible for the valve to be driven via an actuating element with memory effect.

The apparatus according to the invention is expediently arranged in the inner door of a water-carrying household appliance, in particular of a dishwasher, and has a corresponding opening through which the washing liquid can circulate and/or can enter into the chamber region.

Following the chamber region has been filled with washing liquid during the washing phase, a corresponding quantity of washing liquid will adhere to the translucent element, which preferably consists of glass, particularly advantageously of boron silicate, and, when the drying operation commences, will possibly leave behind a corresponding deposit, in other words a lime deposit. The extent of the scale build-up, in particular of the lime deposits, is measured according to the invention via an optical signal. The measurement is based on the following physical phenomenon.

The light (for example infrared light) emitted by the optical-signal-emitting element enters into the translucent element via the first terminating surface and, on account of the reflection taking place in the translucent element, is constantly reflected at the boundary surface between the translucent element and the surroundings, i.e., the enclosing atmosphere. The light beam thus radiates, substantially without refraction and scattering losses, through the translucent element and, finally, passes out through the second terminating surface and enters into the optical-signal-receiving element. The total reflection taking place in the translucent element dictates the brightness value, which corresponds to a certain energy value. A difference in energy between the optical-signal-emitting element and the optical-signal-receiving element is based on a certain radiation capacity of the translucent element and is correspondingly taken into account during processing of the signal value.

When the translucent element is wetted by washing liquid and corresponding deposits, e.g. lime deposits, adhere to the translucent element during the drying operation, the refractive index between the translucent element and the directly adjoining deposit layer changes in these regions such that the number of total reflections at the boundary layer of the translucent element decreases. This is because a light beam impinges at a certain angle on the boundary surface of the translucent element and, if this region of the translucent element is covered by a deposit layer, a certain amount of the light beam passes out of the translucent element and is not reflected into the translucent-element. Total reflection occurs only where the angle of incidence is less than the critical angle. Since the optical-signal-receiving element measures the energy intensity or light intensity of the light passing out of the translucent element, the light intensity received is associated with a corresponding scale build-up, e.g. a lime deposit, on the translucent element.

The apparatus according to the invention can thus determine the beginning of deposit formation on the translucent element, which preferably consists of glass, with the result that appropriate measures, e.g., in the case of lime deposits being established, for water softening, can be taken in good time. According to the invention, deposits, e.g. lime deposits, on the translucent element can already be established before this is visible to the human eye on glassware.

Once a certain deposit-threshold value, in particular one for lime deposits, has been established, the regenerating process for the ion exchanger is started and the normally very thin deposits, in particular lime deposits, on the translucent element are cleaned using newly softened water and possibly washing agent. In order to achieve a reproducible circulating-flow structure in the chamber region, the chamber region has an opening which is preferably designed such that it is not possible for any food residues to penetrate into the chamber region. A lattice-like covering is preferably provided for this purpose, wherein case the respective lattice openings should be dimensioned such that customary, frequently encountered food-residue particles, for example pips of citrus fruits, cannot pass through.

Once the chamber region has been filled with washing liquid, the latter remains in the chamber region for a predetermined period of time, in order for the constituent parts located in the washing liquid, in particular hardness salts dissolved therein, to be given time for depositing on the translucent element. Before emptying the chamber region, the apparatus according to the invention has a valve which is arranged such that the chamber region can be emptied completely. The valve may be formed by conventional magnetic valves or also by valves which can be actuated mechanically. Particularly advantageous valves are ones which can be actuated by actuating elements made of memory metal.

In order realistically to address a depositing process, e.g. the lime-depositing process, as takes place during the drying phase in the dishwashing compartment of the dishwasher, the apparatus according to the invention has a heating element which heats the moist atmosphere in the chamber region and thus dries the translucent element. During this drying process, if water is not fully softened, a lime deposit forms on the translucent element and this lime deposit is determined by way of the above-described measuring process.

Other features which are considered as characteristic for the invention are set forth in the appended claims.

Although the invention is illustrated and described herein as embodied in an apparatus for checking the formation of scale, and water-carrying appliance, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a schematic illustration of the functioning of the translucent element and of the two signal-receiving and signal-emitting elements;

FIGS. 2A and 2B are schematic illustrations of the translucent elements, showing the functional principle of the apparatus according to the invention;

DESCRIPTION OF THE PREFERRED EMBODIMENTS

Figure 3:
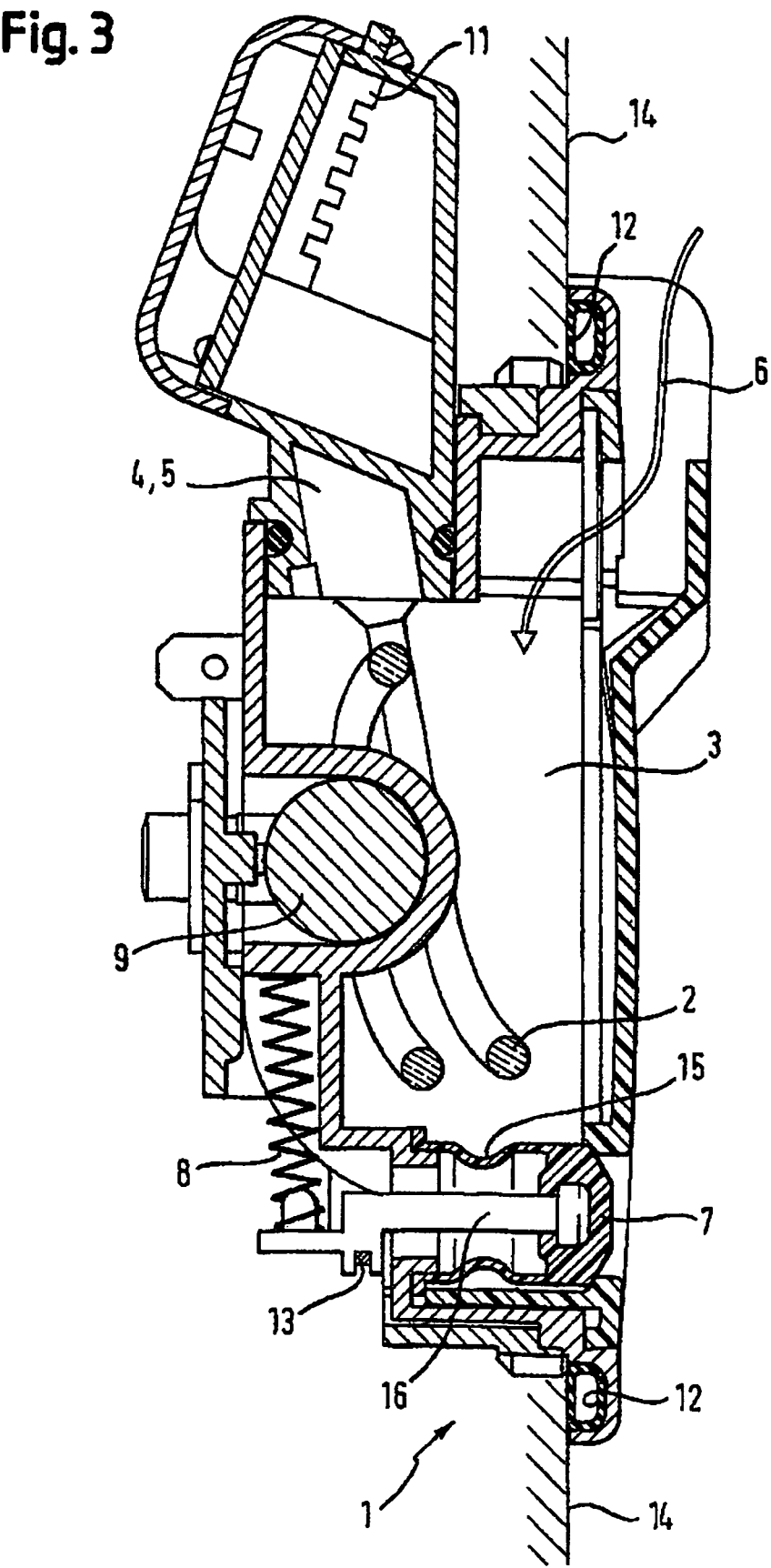
FIG. 3 is a sectional view illustrating a preferred embodiment of the apparatus according to the invention.
Figure 4:
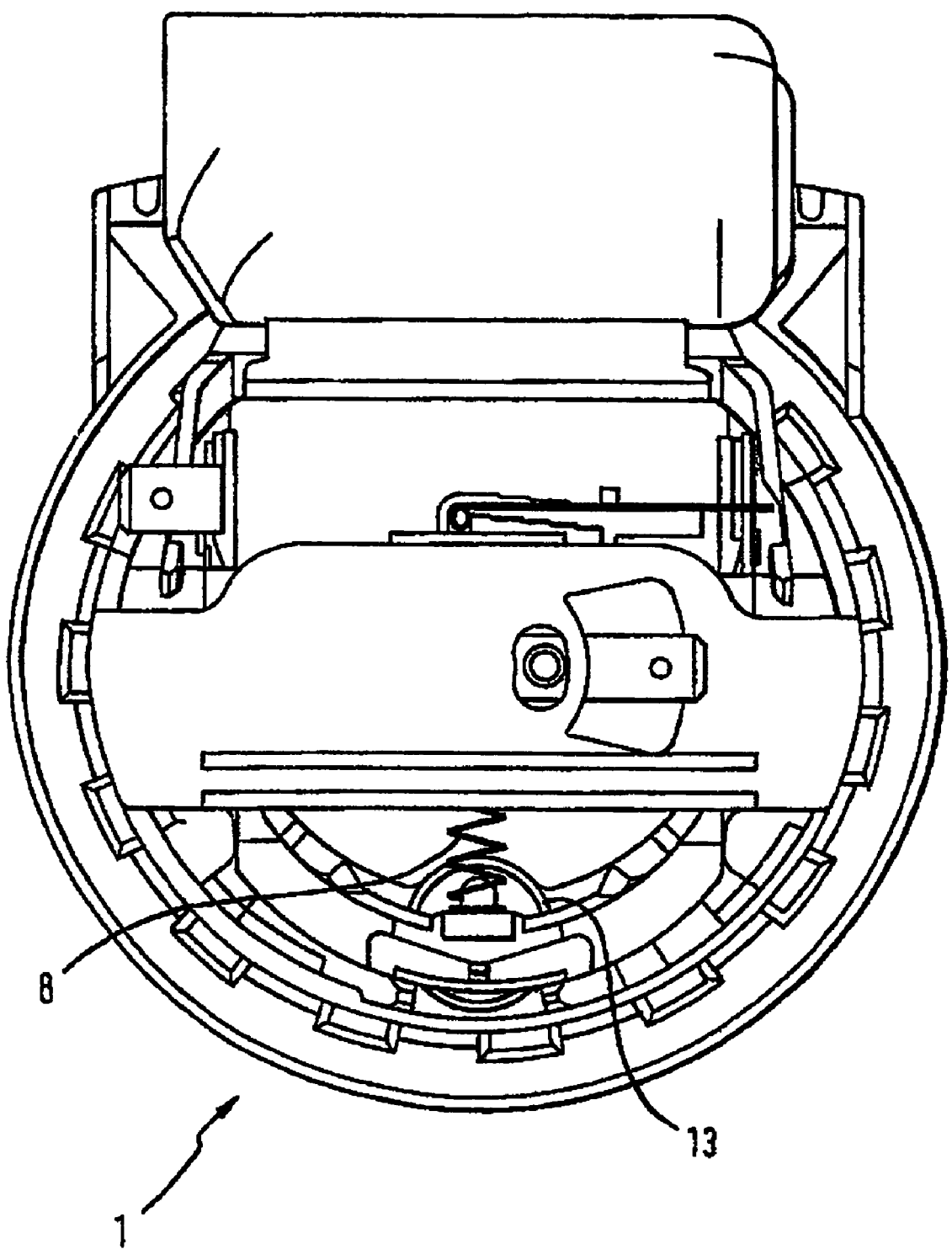
FIG. 4 is an elevational view of the preferred embodiment according to FIG. 3.
Figure 5:
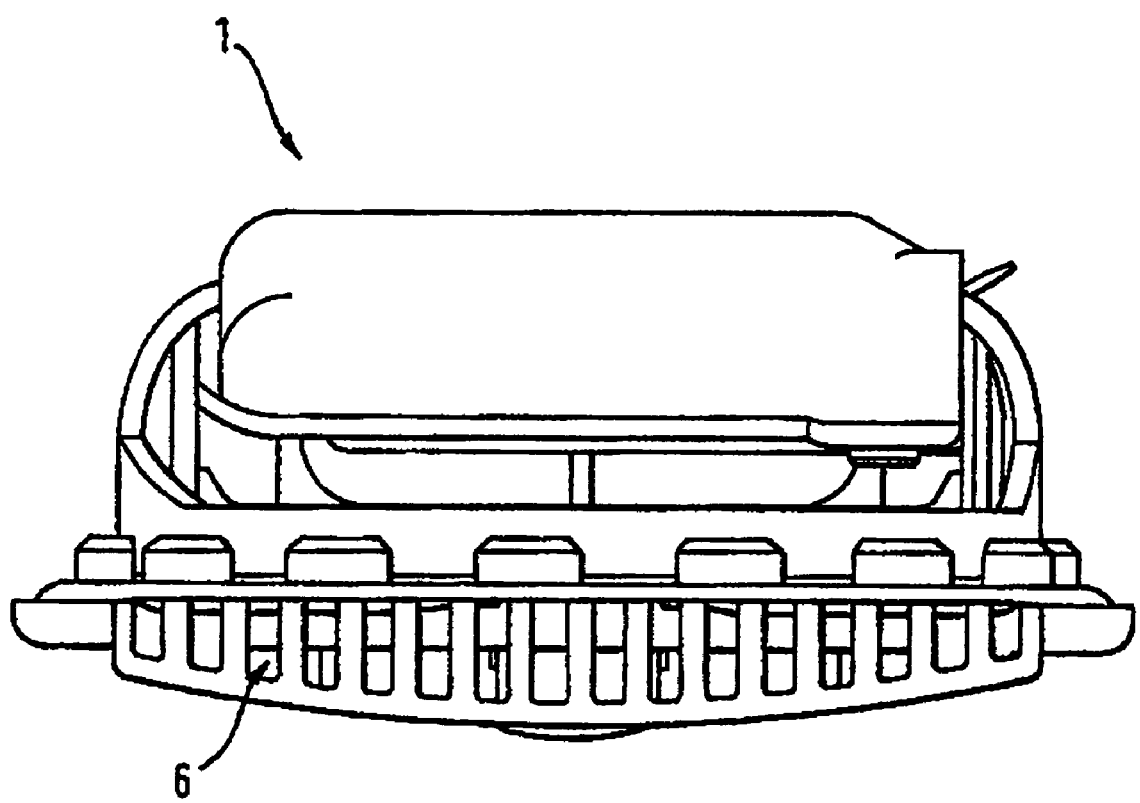
FIG. 5 is a plan view of the preferred embodiment according to FIGS. 3 and 4.

Referring now to the figures of the drawing in detail and first, particularly, to FIG. 1 thereof, there is shown an optical-signal-emitting element 4 and an optical-signal-receiving element 5 connected to one another via a translucent element 2. A U-shape has been selected for the translucent element 2. In the case of the preferred embodiment that is shown in FIGS. 3, 4 and 5, the translucent element is of helical design and thus has the advantage of using a relatively long light-carrying path for measuring purposes. The translucent element may also be designed without any curvature, in particular the design of a rod-like translucent element may be advantageous. If use is made of a rod-like translucent element, it is possible to arrange a plurality of elements one beside the other in the chamber region, in order to achieve, for example, a certain degree of redundancy during the measuring operation. If use is made of a plurality of translucent elements, furthermore, the light spectrum may be selected to be broader. In other words, it is possible to vary the preferred infrared range in the case of the individual translucent elements and the optical-signal-emitting-receiving elements connected thereto.

The physical phenomenon on which the apparatus according to the invention is based is illustrated in FIGS. 2A and 2B. The light emitted by the optical-signal-emitting element 4 has an energy level $E_1$ and, having passed through the translucent element 2, has an energy level $E_2$ at the optical-signal-receiving element 5. If, as illustrated in FIG. 2A, the translucent element 2 does not contain any contamination, such as, lime deposits or other scale build-up, essentially all the light beams which are emitted into the translucent element 2 by the optical-signal-emitting element 4 are reflected on account of the total reflection between the translucent element and the surrounding atmosphere, until the optical-signal-receiving element 5 is reached, and do not leave the translucent element. As a result, the energy level $E_1$ corresponds substantially to the energy level $E_2$, with the result that, upon determination of these two energy levels, it is established that there is no contamination or scale build-up, i.e., lime deposit, on the translucent element 2.

If the translucent element has insufficiently softened water circulating around it, and is then dried, this results in the formation of lime deposits 10 which at least partially cover the outer surface of the translucent element 2. Upon transillumination of the translucent element 2, where the optical-signal-emitting element 4 emits radiation at an energy level $E_3$, the optical-signal-receiving element 5 receives an energy level $E_4$. In correspondence with the lime deposit 10, it can be established that the energy level $E_4$ is significantly lower than the energy level $E_3$. As a result, the determination of the energy level $E_4$ relative to the energy level $E_3$ makes it possible to establish the degree of lime deposit or of contamination on the translucent element 2.

For example, in order to process the energy level $E_4$, the value of the latter is inverted and it is then present as a positive voltage. The program-control unit connected downstream, in a signal flow direction, that is, of the optical-signal-receiving element processes this positive measuring signal and, on account of measurement data provided, derives a corresponding measurement result. Depending on setting and program control, when a threshold value or degree of contamination is reached, regeneration of the ion exchanger is activated, in order thus for softened water of appropriate quality to be available for the next washing-program sequence.

FIG. 3 shows a sectional illustration through a preferred embodiment of the present invention, which is used in a water-carrying household appliance. The apparatus 1 according to the invention is preferably installed in the inner door 14 of a dishwasher (preferably snapped into place and held with circumferentially disposed tabs) and, for sealing between the dishwashing compartment and the inside of the door, is sealed via corresponding sealing elements 12. During the washing program, washing liquid flows, along the arrow direction 6, into the chamber region 3, fills the latter and thus wets the translucent elements 2. The latter have a helical configuration or design. Once wetting has taken place, the chamber region 3 is emptied via the valve 7 and the chamber region 3 is heated by means of heating element 9 such that the wetted translucent element 2 dries. If the wetting operation takes place with insufficiently softened water, a lime deposit forms on the translucent element 2, this deposit being determined by means of the above-described measuring method, using the elements 4, 5. Prior to the drying operation, the chamber region 3 is expediently flooded and emptied a number of times, in order for reproducible results thus to be obtained. The heating element 9 used is preferably a so-called PTC (Positive Temperature Coefficient) element, which forms certain flow characteristics and is capable of heating the chamber region 3 to a uniform temperature of, for example, above 100° C. A so-called memory wire 13 is provided for actuating the valve in the preferred embodiment according to FIG. 3, this memory wire changing shape when heated, i.e. when a certain current flows through, and opening the valve 7. The valve 7 expediently comprises an elastomeric region 15 and a pin-like element 16 which, on account of the change in shape of the memory wire 13, changes its position and thus opens the valve 7. Following cooling of the memory wire 13, the force applied by the restoring spring 8 predominates, and moves the pin 16, together with the elastomeric region 15, such that the valve 7 is closed.

The rear view of the apparatus according to the invention which is seen in FIG. 4 illustrates the memory wire 13 and the restoring spring 8. The figure further illustrates the preferred round configuration of the apparatus 1 according to the invention.

FIG. 5 shows a top view of the apparatus 1 according to the invention, an illustration being given, in particular, of the chamber region of the opening 6. The region is advantageously designed and dimensioned such that food residues cannot pass into the chamber region 3 of the apparatus 1 according to the invention.

The present invention provides an apparatus 1 which makes it possible to determine the formation of scale, e.g. the degree of water hardness, or a tendency towards the formation of scale, e.g. the degree of water hardness, and to achieve corresponding measures for setting the desired formation of scale, e.g. the desired degree of water hardness.

We claim:

1. An apparatus for configured for determining a scale build-up in an appliance, comprising:
    a translucent element formed with first and second terminating surfaces and having a chamber region;
    at least one optical-signal-emitting element disposed at and directly adjoining said first terminating surface;
    at least one optical-signal-receiving element disposed at and adjoining said second terminating surface, wherein said terminating surfaces are disposed to not be subject to scale deposits; and
    a valve disposed to selectively empty a chamber region surrounding said translucent element, and a heating element commonly operating said valve and drying said translucent element.

2. An apparatus for checking a formation of scale, comprising:
    a translucent element formed with first and second terminating surfaces;
    at least one optical-signal-emitting element disposed at and directly adjoining said first terminating surface, said translucent element forming a light carrying path between its first and second terminating surfaces operable along which travels light emitted by said at least one optical-signal-emitting element;
    at least one optical-signal-receiving element disposed at and adjoining said second terminating surface, wherein said terminating surfaces of said translucent element are disposed to not be subject to scale deposits; and
    means for alternately disposing said translucent element in a wetting condition in which said translucent element is wetted by a washing liquid and a deposition condition in which contact between said translucent element and the washing liquid is controlled to effect the deposition of scale on said translucent element, said at least one optical-signal-emitting element being operable, in the deposition condition of said translucent element, to emit light that travels along said light carrying path of said translucent element and said at least one optical-signal-receiving element being operable, in the deposition condition of said translucent element, to receive light emitted by said at least one optical-signal-emitting element that has traveled along said light carrying path of said translucent element.

3. The apparatus according to claim 2, wherein said translucent element is a selected one of a rod-shaped element having a helical form and a rod-shaped element having a non-helical form.

4. The apparatus according to claim 2, wherein said means for alternately disposing said translucent element in a wetting condition and a deposition condition includes a chamber region in which said translucent element is located.

5. The apparatus according to claim 4, wherein the water-carrying appliance is a household appliance and said chamber region is formed with at least one opening open into an interior of the household appliance.

6. The apparatus according to claim 5, said means for alternately disposing said translucent element in a wetting condition and a deposition condition includes a valve disposed at said chamber region for selectively emptying said chamber region.

7. A dishwasher, comprising:
  means for carrying water in which items to be washed can be disposed; and
  an apparatus for checking a formation of scale having:
  (a) a translucent element formed with first and second terminating surfaces,
  (b) at least one optical-signal-emitting element disposed at and directly adjoining said first terminating surface, said translucent element forming a light carrying path between its first and second terminating surfaces operable along which travels light emitted by said at least one optical-signal-emitting element,
  (c) at least one optical-signal-receiving element disposed at and adjoining said second terminating surface, wherein said terminating surfaces of said translucent element are disposed to not be subject to scale deposits, and
  (d) means for alternately disposing said translucent element in a wetted condition in which said translucent element is wetted by a washing liquid and a deposition condition in which contact between said translucent element and the washing liquid is controlled such that scale forming matter in the washing liquid is deposited as scale on said translucent element and the scale thus deposited on said translucent element is not carried away by the washing liquid, said at least one optical-signal-emitting element being operable, in the deposition condition of said translucent element, to emit light that travels along said light carrying path of said translucent element and said at least one optical-signal-receiving element being operable, in the deposition condition of said translucent element, to receive light emitted by said at least one optical-signal-emitting element that has traveled along said light carrying path of said translucent element.

8. The apparatus according to claim 7, wherein said means for alternately disposing said translucent element in a wetted condition and a deposition condition controls the wetting of said translucent element during said wetted condition such that the washing liquid carries away from said translucent element at least a portion of the scale that had been deposited on said translucent element during an earlier disposition of said translucent element in its deposition condition.

* * * * *